(12) United States Patent
Schneider et al.

(10) Patent No.: US 7,046,364 B2
(45) Date of Patent: May 16, 2006

(54) METHOD AND APPARATUS FOR MATCHING GLOSS LEVELS OF PRINTED AND UNPRINTED REGIONS OF A MEDIA SUBSTRATE

(75) Inventors: Eric Schneider, Boise, ID (US); Santiago Rodriguez, Boise, ID (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 308 days.

(21) Appl. No.: 10/388,886

(22) Filed: Mar. 14, 2003

(65) Prior Publication Data

US 2004/0179201 A1    Sep. 16, 2004

(51) Int. Cl.
    G01N 21/47    (2006.01)
    G03G 15/20    (2006.01)

(52) U.S. Cl. .................... 356/446; 399/67; 399/69

(58) Field of Classification Search ........ 356/445–448; 399/38, 67, 69
    See application file for complete search history.

(56) References Cited

U.S. PATENT DOCUMENTS

| | | | |
|---|---|---|---|
| 5,748,221 A * | 5/1998 | Castelli et al. | 347/232 |
| 5,925,889 A | 7/1999 | Guillory et al. | |
| 6,006,668 A | 12/1999 | Rehmann | |
| 6,101,345 A | 8/2000 | Van Goethem et al. | |
| 6,271,870 B1 | 8/2001 | Jacob et al. | |
| 6,325,505 B1 | 12/2001 | Walker | |
| 6,819,886 B1 * | 11/2004 | Runkowske et al. | 399/38 |

* cited by examiner

Primary Examiner—Richard A. Rosenberger

(57) ABSTRACT

A method and apparatus for matching the gloss level of a printed region of a media substrate surface to the gloss level of a non-printed region of the media substrate surface are provided. Optical reflection intensities are measured in both printed and non-printed regions of the media substrate surface and read by a gloss sensing device which communicates the intensities to a printer controller. The printer controller compares the reflection intensities for the two regions to determine if they are substantially equivalent. If they are not substantially equivalent, the printer controller instructs alterations in printing parameters, e.g., temperature and/or pressure of fuser rollers, in an effort to establish equivalence.

13 Claims, 2 Drawing Sheets

Figure 1:
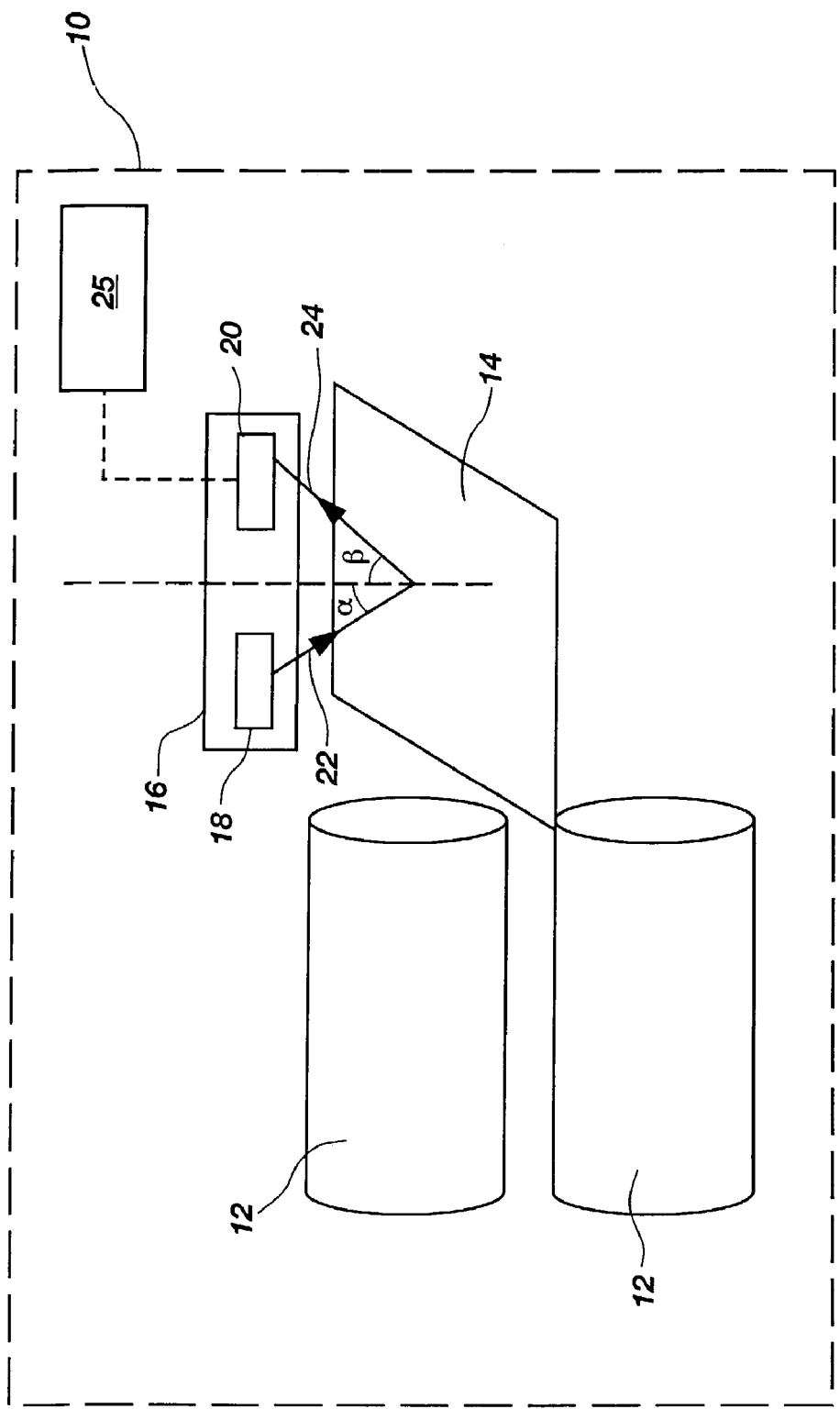

METHOD AND APPARATUS FOR MATCHING GLOSS LEVELS OF PRINTED AND UNPRINTED REGIONS OF A MEDIA SUBSTRATE

FIELD OF THE INVENTION

The present invention relates generally to thermally-fixed printing processes and to printing mechanisms utilizing such processes. More specifically, the present invention relates to a sensor system and method for determining and evaluating information about the gloss level of an image-receiving media substrate and of an image printed thereon in order to match the gloss level of toner fused to the media substrate to the gloss level of the media substrate itself.

BACKGROUND OF THE INVENTION

Printing devices, such as laser printers, use a printing composition (e.g., ink or toner) to print text, graphics, images and the like onto a media substrate. Laser printing processes utilizing such devices employ static electricity to secure images to the substrate. A photoreceptor or drum in the printing device, which is formed of a highly photoconductive material, is given a positive charge by a wire having an electrical current running therethrough. Once the surface of the drum is charged, a laser beam shines across the charged photoreceptor surface to discharge certain regions thereof. In this way, the desired image is formed, temporarily, on the surface of the photoreceptor. Such image is often referred to as an "electrostatic image". Once the electrostatic image is formed, the photoreceptor is coated with positively charged toner which clings to the negative discharged regions of the drum. With the toner pattern affixed, the drum rolls over a media substrate having a negative charge which is moving along on a belt below the drum at substantially the same speed at which the drum is rotating. The negative charge of the media substrate is stronger than that of the electrostatic image and, thus, the media substrate pulls the toner away from the photoreceptor and an exact duplicate of the electrostatic image is formed on the substrate surface.

Once all of the toner has been passed to the media substrate, it is directed through a fusing station, which is typically a pair of heated rollers. As the substrate passes through the rollers, the toner melts, fusing with the fibers in the media substrate. The paper is then passed into the printer output tray and printing of the desired image is complete.

The quality of the image formed on a media substrate as just described depends on a number of factors, including the surface characteristics of the substrate itself. Various media substrates may be used in the laser printing process including, but not limited to, letter quality paper, envelopes, photographic print stock, transparencies and the like. Some media substrates have a finish on the surface thereof which is glossy (e.g., transparencies and photographic print stock) while other substrates have a finish which is matte (e.g., envelopes and letter quality paper). The terms "glossy" and "matte" refer generally to the amount of light which is reflected from the surface of the substrate when it is illuminated by a light source, with glossy media substrates reflecting more light than matte media substrates. In order to achieve optimal printed output, whether a media substrate is glossy or matte, and the level of gloss reflected therefrom, should be determined and taken into account during printing and the printing parameters set accordingly.

The gloss level of a media substrate on which printing is desired may be accounted for in the printing process by a user manually adjusting the printing device in accordance with the determined gloss level. For instance, a user may be presented with options to input whether the media is glossy or matte, or may be prompted to select the particular media substrate type from a pre-established list of media substrate types for which the level of gloss is defined and stored by a printer driver or controller. This method may be undesirable, however, in that users are often unable to differentiate between glossy and matte substrate finishes and/or may be unaware of the type of media substrate being used. If the media characteristics are incorrectly input, an optimal printed output may not be achieved.

Several methods have been proposed by which the above-stated drawbacks to user intervention in the printing process may be alleviated. For instance, a method has been disclosed for differentiating between glossy-finish and matte-finish print media by detecting whether a reflected light signal is polarized or unpolarized. Sheets of print media having a matte-finish reflect unpolarized light signals and sheets of print media having a glossy-finish reflect polarized light signals. Thereafter, the media detector communicates a signal to a controller coupled to the media detector and the controller adjusts the printing device for printing on glossy-finish print media or matte-finish print media based on the signal received from the media detector.

Another method for determining gloss level of a media substrate with little or no user intervention is a method for determining, based upon gloss level, the media type of a sheet of print media prior to printing. In the method, a reference surface is illuminated and the spectral reflection intensity is measured by a sensor and assigned a first value. Subsequently, a media sheet is moved onto the reference surface, the sheet is illuminated and the spectral reflection intensity is measured by a sensor and assigned a second value. The ratio of the first spectral reflection intensity to the second spectral reflection intensity is compared to a threshold value selected from a set of predetermined threshold values to identify the media by gloss level.

In another method, a system of classifying the type of media to be printed upon in an inkjet printing mechanism is provided. A portion of a print media is scanned several times to generate a collection of reflectance values which are then averaged to determine a classification value. The classification value is then analyzed through comparison with known values for different types of media to classify the print media as one of the pre-defined types.

In order to achieve a substantially optimal printed output, the toner fused to the media substrate should have substantially the same gloss level as the unprinted surface of the media substrate itself. Thus, once the media substrate gloss level is determined and input into, or otherwise communicated to, the printer driver or controller, the printing parameters may be adjusted in an effort to match the gloss level of the toner to that of the media substrate. Commonly adjusted printing parameters include the temperature of the fuser rollers and the fuser pressure. If the gloss level of the media substrate is high, the temperature of the fuser rollers may be increased and/or the fuser pressure increased to produce a glossy image thereon. Alternatively, if the gloss level of the media substrate is low, the temperature of the fuser rollers may be decreased and/or the fuser pressure decreased to produce a matte image. Exactly how high the temperature or how the pressure of the rollers is to be adjusted is generally predetermined and stored in the printer controller with certain parameters corresponding to certain media types; the media types also being predetermined and stored as discussed with the prior art methods, above.

One method for achieving a pre-selected gloss level by choosing the appropriate fuser temperature is, the method of establishing a gloss value for a pre-defined gloss and, subsequently, selecting a fusing temperature and fusing period in accordance with the gloss value. The fusing temperature and/or rotation speed of at least one fuser roller is then controlled within the defined temperature and fusing period ranges. Stated differently, a user selects the desired gloss level from a pre-defined set of gloss levels, inputs the desired level into a controller and a microprocessor subsequently sets the fusing temperature and period parameters to achieve the desired gloss level. The microprocessor may take into account other factors, such as the paper thickness, the toner type, the paper weight, the humidity and the rigidity of the paper, in establishing the parameter selections.

In each of the above described methods, the gloss level of the desired media substrate is determined and subsequently compared to a predetermined and predefined list of media substrates. The user or the printer controller determines which substrate type gloss level from the predefined list most closely approximates the gloss level of the substrate on which printing is desired and adjusts the printing parameters in accordance with parameters predetermined and stored as associated with the predefined substrate. These methods still may not achieve optimal print output as the media selections are based on a finite number of predetermined thresholds. Thus, if the media on which printing is desired is not among those having printing parameters predefined and stored in the printer controller, an approximation must still be made and the parameters set to maximize printing for that media substrate having a gloss level which most closely approximates that of the substrate to be printed.

Accordingly, a method and device for optimizing print output by accurately matching the gloss level of printed and unprinted regions of a media substrate would be advantageous. Further, a method and device which permits customization of printing parameters to any desired media substrate would be desirable.

BRIEF SUMMARY OF THE INVENTION

The present invention includes a method and apparatus for matching the gloss level of a printed image on a media substrate surface to the gloss level of an unprinted portion of the media substrate surface is disclosed.

In one embodiment of the method of the present invention, a print file that is resident in the printer memory is selected. The print file contains the appropriate coding for a customized print pattern. Printing is initiated with media being drawn from the appropriate feed tray in which the media substrate on which printing is desired is contained. The media proceeds through the printer, including through the fusing station, and exits the printer into the printer output tray. As the media exits the printer fusing station, a gloss sensor takes readings of the gloss levels of both the printed test patches and the unprinted regions of the media substrate surface. These readings are communicated to the printer controller. If the readings taken in the two regions are not substantially identical, the printer controller instructs changes to the printing parameters to be made by an associated microprocessor.

An apparatus of the present invention is used for matching the gloss level of a printed image on a media substrate surface to the gloss level of an unprinted portion of the media substrate surface in accordance with the method of the present invention.

Other features and advantages of the present invention will become apparent to those of ordinary skill in the art through a consideration of the ensuing description, the accompanying drawings and the appended claims.

BRIEF DESCRIPTION OF THE SEVERAL
VIEWS OF THE DRAWINGS

Figure 2:
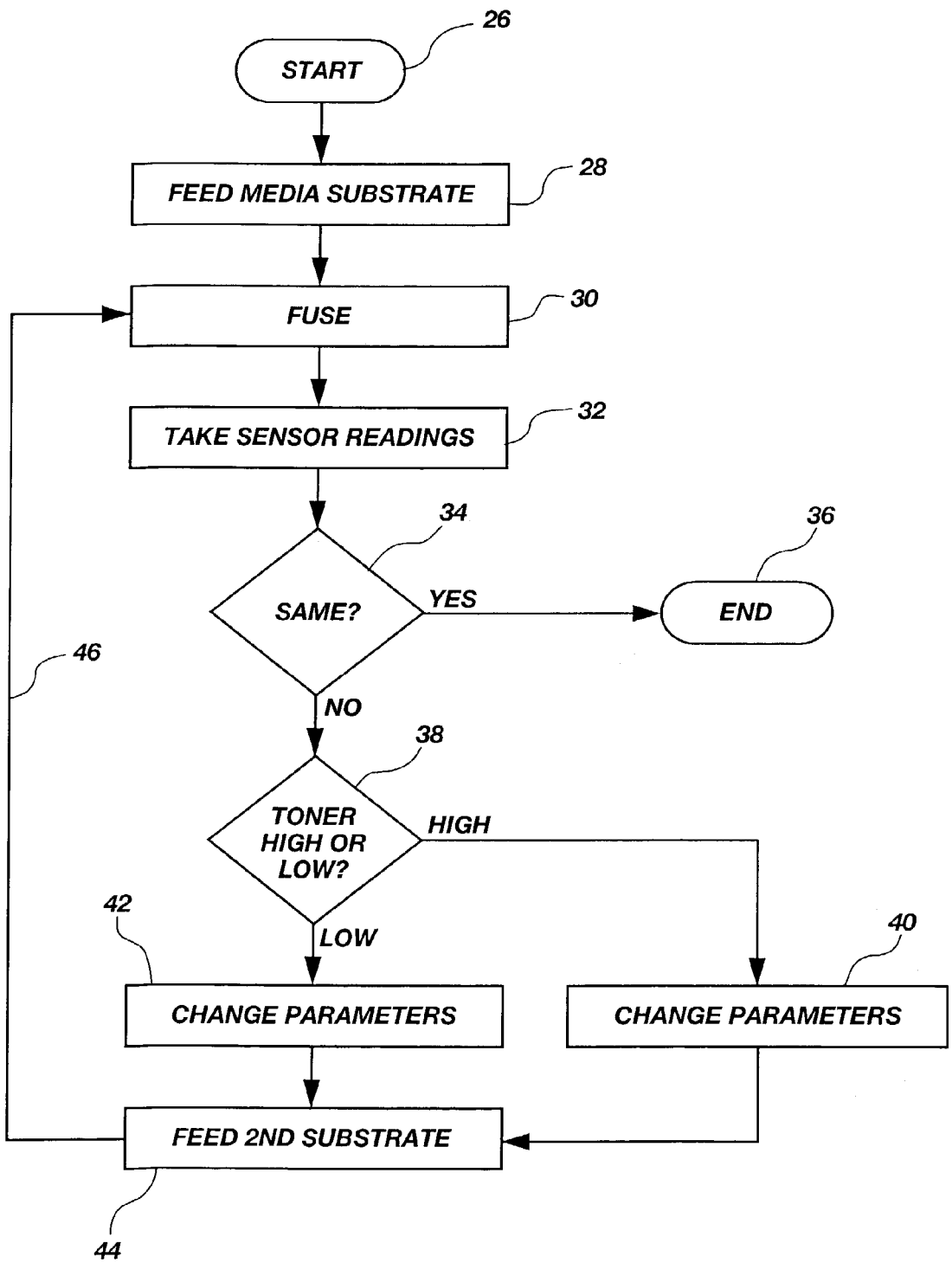

While the specification concludes with claims particularly pointing out and distinctly claiming that which is regarded as the present invention, the present invention can be more readily ascertained from the following description of the invention when read in conjunction with the accompanying drawings in which like reference numerals refer to like parts in the various views and in which:

FIG. 1 is a schematic view of an embodiment of the invention showing a portion of an apparatus (e.g., a printer) having a gloss level sensing system according to the present invention; and FIG. 2 is a flow chart depicting a method for matching the gloss level of a printed image on a media substrate to the gloss level of an unprinted portion of the media substrate in accordance with an embodiment of the present invention.

DETAILED DESCRIPTION OF THE
INVENTION

The present invention is directed to thermally-fixed printing processes and to printing mechanisms and apparatus utilizing such processes. More specifically, a method and apparatus for matching the gloss level of a printed image on a media substrate surface to the gloss level of an unprinted portion of the media substrate surface are provided. The particular embodiments described herein are intended in all respects to be illustrative rather than restrictive. Alternative embodiments will become apparent to those of ordinary skill in the art to which the present invention pertains without departing from its scope.

Referring to the figures in general and initially to FIG. 1 in particular, an embodiment of a printing device 10 employing principles of the present invention is illustrated. Many conventional components of the printing device 10 are omitted from FIG. 1 in an effort to maintain clarity of description with respect to those elements which more directly relate to the method and apparatus of the present invention. It will be understood and appreciated by those of ordinary skill in the art that the printing device 10 may be used for any conventional home, office, or industrial purpose, or in any other environment.

The printing device 10 includes a pair of heated fuser rollers 12 between which a media substrate 14 may be passed in order to fuse a printing composition (e.g., toner) to the media substrate 14 and form an image thereon. Such fusing processes are known to those of ordinary skill in the art and, thus, will not be further described herein. The printing device 10 also includes a gloss level sensing system, generally referred to by reference numeral 16, which includes a light source 18 (e.g., a light emitting diode (LED)) and a gloss sensing device 20. In use, the light source 18 directs light toward the media substrate 14 in a first direction, represented by arrow 22. The light is reflected from the media substrate 14 in a second direction, represented by arrow 24, toward the gloss sensing device 20 which measures the intensity of reflection and communicates such measurement to a printer controller 25, as more fully described below. Typically, the light source will direct light toward a single sheet of the media substrate 14 approximately twenty times, each time reflecting the light from a different region of the media substrate 14 and, thus, generating approximately twenty sensor readings from each media substrate sheet 14.

The printing device 10 also includes a printer controller 25 that receives instructions from an external device, typically a personal computer (not shown), through a communications port (not shown). Many of the printer controller functions may be performed by the external device or by the electronics resident in the printing device 10. Alternatively, printer controller functions may be performed by interactions between the external device (not shown) and the printing device 10. As used herein, the term "printer controller" is intended to encompass all functions thereof, whether performed by the external device, the printing device 10 itself, or an interaction therebetween.

The gloss sensing device 20 may be coupled to the printer controller 25 such that the gloss sensing device 20 may communicate signals derived from the reflectance readings thereto. The printer controller 25 then may examine the received information and instruct a microprocessor (not shown) to adjust the printing parameters accordingly. This process is more fully described herein as it relates to the practice of the method of the present invention.

The method of the present invention comprises a gloss optimization process. Initiation of the gloss optimization process results in a substantially optimal printed output, as more fully described below. Before the gloss optimization process may be initiated, a couple of initial items should take place. One such item is selection and appropriate placement of the media substrate type on which printing is desired. Such selection is typically made by the user. Once a user selects the desired media substrate type, a plurality of media substrate sheets 14 are placed into the appropriate feed tray (not shown) of the printing device 10. Media substrate sheets 14 may be any media substrate type compatible with the printing device 10 including, but not limited to, letter quality paper, envelopes, photographic print stock, transparencies, card-stock paper and the like.

As a second initial item to take place prior to initiation of the gloss optimization process, the user may select the "gloss optimization" function from the printer control panel. For example, the user may select "Initiate Gloss Test", or any other such indicator, from the menu of the printer control panel. Alternatively, the gloss optimization function may be selected by the user through a graphical user interface (GUI) in the printer driver (not shown) using conventional methods as known to those of ordinary skill in the art.

The user also may select the print mode as per usual, which sets parameters such as print engine speeds and conditions for printing. In one embodiment, a user may select one of a predefined set of stored media types as a condition for printing so as to set initial printing conditions at a close approximation to the media substrate 14 on which printing is desired. In this embodiment, the gloss optimization function may be completed more quickly as the adjustments that need to be made may be less substantial.

It will be understood and appreciated by those of ordinary skill in the art that the above-stated substrate selection and loading, print mode selection and gloss optimization function selection steps may be performed in any order, so long as each is completed prior to initiation of printing.

The gloss optimization method of the present invention begins with initiation of printing (again by the user selecting a function indicator from either the printer control panel or through a GUI) as indicated by reference numeral 26 of FIG. 2. Such initiation causes a print file that is resident in the printer memory (or in an external device associated with the printer, if desired) to be selected. The print file contains the appropriate coding for a customized print pattern which includes a number of test patches. It is currently preferred that both cmyk (cyan-magenta-yellow-black) and rgb (red-green-blue) test patches are contained in the customized print pattern.

Printing is initiated with the media substrate 14 being drawn from the appropriate feed tray (not shown) of a printing device 10 in which the media substrate 14 on which printing is desired is contained. The media substrate 14 is fed through a printer, as indicated by reference numeral 28, and proceeds to the printer fusing station of the printing device 10 wherein the printing composition is fused to the media substrate 14. Such is illustrated as reference numeral 30. The media substrate 14 then exits near the fuser rollers 12 of the printing device 10. As the media substrate 14 exits the fusing station, it encounters gloss level sensing system 16 of the printing device 10. The gloss level sensing system 16 begins to take gloss readings to feed back to the printer controller 25 such that gloss adjustments may be made, as indicated by reference numeral 32.

To take an initial reading, a light emitting diode (LED) 18 of the printing device 10, or any suitable light source, directs a beam of light toward a first region of the surface of the media substrate 14 at an angle of incidence, $\alpha$. The light is reflected from the surface of the media substrate 14 at an angle of reflection, $\beta$, toward gloss sensing device 20 of the printing device 10. The angle of reflection, $\beta$, is equivalent to the angle of incidence $\alpha$. Gloss sensing device 20 receives the reflected light and communicates a signal to the printer controller 25, the signal being indicative of the intensity of the light received. The printer controller 25 stores the signal therein. Alternatively, the signal may be stored in an external device (not shown) associated with the printer controller 25. The light source 18 (LED) then directs a second beam of light toward a second, different region of the surface of media substrate 14. The light again strikes the surface of the media substrate 14 at an angle of incidence, $\alpha$, and the light is reflected toward gloss sensing device 20 at an angle of reflection $\beta$ equal to the angle of incidence $\alpha$. The gloss sensing device 20 of the printing device 10 receives the reflected light and communicates a signal indicative of the intensity thereof to the printer controller 25 where the signal is again stored.

If the media substrate 14 upon which gloss readings are being taken has a medium gloss level, the light source 18 may be mounted at approximately 75° off media normal or 15° from the plane of the media substrate 14 surface. Stated differently, the light source 18 directs a beam of light toward the surface of the media substrate 14 at a 75° angle of incidence. Accordingly, the light reflected back toward the gloss sensing device 20 is reflected at a 75° angle of reflection. If the media substrate 14 upon which gloss readings are being taken has a high gloss level, the angles of incidence and reflection will be less than 75°. Conversely, if the media substrate 14 has a low gloss level, the angles of incidence and reflection will be greater than 75°.

As the angles of incidence and reflection do not change for each beam of light directed toward a particular sheet of the media substrate 14, it is apparent that in order for each reading to be taken at a different point on the media substrate 14 surface, such readings are taken in a line which follows the direction in which the media substrate 14 is fed through the printing device 10. As such, the test patches of the customized print pattern are aligned in the direction of movement, with nonprinted regions positioned therebetween. In this way, readings may be taken in the cmyk and rgb test patches, as well as in the nonprinted portions of the media substrate 14, without the angle at which LED 18 is mounted being altered. It will be understood by those of ordinary skill in the art, however, that if the test patches were present in some other arrangement wherein reading from the various regions would be facilitated by a change in the mounting angle, such variable may also be changed upon instruction from the printer controller 25. The angles of incidence and reflection would accordingly have to be altered to maximize the accuracy of the reflectance signal.

The above process is repeated multiple times, typically approximately twenty. The readings stored in the printer controller 25 are subsequently compared, as illustrated by reference numeral 34. All of the signals stored by the printer controller 25 are compared in an effort to determine whether the signals received from printed regions have a higher or lower reflectance than those received from non-printed regions of the media substrate 14. An algorithm typically may be employed in an effort to normalize the readings from each of the printed and unprinted regions, e.g., the values in each region may be averaged.

If the values are the same, the gloss optimization mode is complete and the process comes to an end, as indicated by reference numeral 36. Printing may then begin of the desired files (text, graphical images and the like) with a substantially optimal print outcome being achieved. Alternatively, if the reflectance values in the printed and unprinted regions are not equal, the printer controller 25 of the printing device 10 instructs the microprocessor (not shown) associated therewith to make adjustments to the printing process. For instance, if the reflectance value of the unprinted regions exceeds that of the printed regions, the printer controller may instruct the microprocessor to increase the temperature and/or pressure of the fuser rollers 12. This is indicated by reference numeral 40. Conversely, if the reflectance value of the unprinted regions is below that of the printed regions, the printer controller may instruct the microprocessor to decrease the temperature and/or pressure of the fuser rollers 12, as indicated by reference numeral 42.

Once appropriate adjustments have been instructed, a second media substrate sheet 14 is fed through the printing device 10 and the process repeated as shown by reference numeral 46. As there is a certain time delay between taking the first readings, communicating those readings to the printer controller 25 and the printing parameters being modified accordingly, typically, approximately twenty test pages may be run through the printer before an accurate matching of gloss levels is achieved.

Once the gloss levels have been substantially matched, the printing parameters may be stored by the user as associated with the particular media type so that print optimization will not have to be performed with the same media again. This may be performed through an Intelligent Driver Interface (IDI) or the like, as known to those of ordinary skill in the art. Of course, as gloss levels may differ slightly among different batches of the same media, it would be prudent for a user to initiate the gloss optimization mode each time the substrate in the appropriate feed tray is changed. If printing is desired on a media substrate type for which gloss optimization has previously been performed, the saved printing parameters may be selected as a starting point, as previously discussed, such that any changes thereto may be insubstantial and the process may be quickly completed.

Although the method of the present invention has been discussed herein as a black-and-white laser printer employing single-sided printing, it will be understood by those of ordinary skill in the art that the present invention is equally applicable to other thermally-fixed printing devices and processes, as well as to printing devices having color printing capability. It will be understood by those of skill in the art that if employed with a color printing process, test patches of various colors may be aligned on the print file resident in the printer and reflectance values taken at each so as to optimize gloss levels for each color. Further, it will be understood that the methods of the present invention may be utilized for single or dual heated fuser roller configurations, as well as to duplex printing processes. It will be further understood that if a duplex printing process is employed, gloss levels on the same media substrate type may be slightly different than with single-sided printing in order to optimize gloss equivalence on both sides. Therefore, if printing parameters are stored as associated with a particular media type, it would be prudent also to indicate whether such parameters are associated with single-sided or duplex printing.

In conclusion, the present invention comprises a method and apparatus for matching the gloss level of a printed image on a media substrate surface to the gloss level of an unprinted portion of the media substrate surface. The method and apparatus of the present invention provide a substantially optimal printed output as the gloss level of the image may be customized to substantially approximate the gloss level of the media substrate upon which printing is desired. Customization also permits other factors, such as media weight, toner type and media thickness, to be taken into account further optimizing the printed output.

Having set forth preferred embodiments of the invention, it is anticipated that suitable modifications may be made thereto by individuals skilled in the art which nonetheless remain within the scope of the invention. For example, the invention shall not be limited to any particular printing compositions, printing devices, or printing technologies. In this regard, the present invention shall only be construed in accordance with the following claims.

What is claimed is:

1. A method for use in an apparatus having at least one fuser roller for matching a first gloss level of a media substrate to a second gloss level of said media substrate, comprising:

printing a pattern on a surface of said media substrate;

establishing, via a first light pulse, a first optical reflectance value indicative of said first gloss level of said pattern on said surface of said media substrate;

establishing, via a second light pulse, a second optical reflectance value indicative of said second gloss level of said media substrate having no pattern located thereon;

comparing said first optical reflectance value and said second optical reflectance value to determine if said first and second values are substantially equivalent; and adjusting at least one of the temperature of said at least one fuser roller and the pressure of said at least one fuser roller when said first gloss level and said second gloss level are not substantially equivalent.

2. The method of claim 1, wherein if said first optical reflectance value is greater than said second optical reflectance value, said adjusting at least one of the temperature of said at least one fuser roller and the pressure of said at least one fuser roller comprises at least one of decreasing the temperature of said at least one fuser roller and decreasing the pressure of said at least one fuser roller.

3. The method of claim 1, wherein if said first optical reflectance value is lesser than said second optical reflectance value, adjusting at least one of the temperature of said at least one fuser roller and the pressure of said at least one fuser roller comprises at least one of increasing the temperature of said at least one fuser roller and increasing the pressure of said at least one fuser roller.

4. The method of claim 1, wherein establishing said first optical reflectance value comprises:
   directing a beam of light toward a first printed region of said media substrate at a first angle; and
   reflecting said beam of light toward a gloss sensing device at a second angle equal to said first angle, wherein said gloss sensing device is capable of reading an intensity of said reflected beam of light, said intensity being indicative of said first optical reflectance value.

5. The method of claim 1, wherein establishing said second optical reflectance value comprises:
   directing a beam of light toward a first non-printed region of said media substrate at a first angle; and
   reflecting said beam of light toward a gloss sensing device at a second angle equal to said first angle, said gloss sensing device reading an intensity of said reflected beam of light, said intensity being indicative of said second optical reflectance value.

6. The method of claim 1, wherein establishing said first optical reflectance value comprises:
   directing a first beam of light toward a first printed region of said media substrate at a first angle;
   reflecting said first beam of light toward a gloss sensing device at a second angle equal to said first angle, said gloss sensing device reading a first intensity of said reflected first beam of light;
   directing a second beam of light toward a second printed region of said media substrate at said first angle;
   reflecting said second beam of light toward a gloss sensing device at a second angle equal to said first angle, said gloss sensing device reading a second intensity of said reflected second beam of light; and
   normalizing said first intensity and said second intensity to produce an overall intensity which is indicative of said first optical reflectance value.

7. The method of claim 1, wherein establishing said second optical reflectance value comprises:
   directing a first beam of light toward a first non-printed region of said media substrate at a first angle;
   reflecting said first beam of light toward a gloss sensing device at a second angle equal to said first angle, said gloss sensing device reading a first intensity of said reflected first beam of light;
   directing a second beam of light toward a second non-printed region of said media substrate at said first angle;
   reflecting said second beam of light toward a gloss sensing device at a second angle equal to said first angle, said gloss sensing device reading a second intensity of said reflected second beam of light; and
   normalizing said first intensity and said second intensity to produce an overall intensity which is indicative of said second optical reflectance value.

8. An apparatus for use in a printing process, said apparatus capable of matching a gloss level of printed regions of a media substrate to a gloss level of non-printed regions of said media substrate, comprising:
   at least one roller having an exit region;
   a light source positioned at said roller exit region;
   a gloss sensing device located after said light source at said roller exit region, said gloss sensing device reading separate light reflection intensities generated by separate light beams from said printed regions of said media substrate and said non-printed regions of said media substrate; and
   a controller coupled with said gloss sensing device receiving and storing said separate light reflection intensities read by said gloss sensing device and instructing alterations in at least one printing parameter when said separate light reflection intensities generated by separate light beams from said printed regions of said media substrate and said non-printed regions of said media substrate are not substantially equivalent, said printing parameter comprising at least one of temperature of said at least one roller and pressure of said at least one roller.

9. The apparatus of claim 8, wherein said light source is a light emitting diode.

10. The apparatus of claim 8, wherein the mounting angle of said light source and said gloss sensing device may be altered by said controller.

11. A method for use with a printing device utilizing a printing process, said method for adjusting at least one of the temperature of a roller and the pressure of said roller in order to match gloss levels on printed and non-printed regions of a media substrate, comprising:
   directing a sheet of said media substrate through said printing device;
   directing a first beam of light toward a first printed region of said media substrate, said first beam of light reflecting toward a gloss sensing device at a first intensity;
   directing a second beam of light toward a first non-printed region of said media substrate, said second beam of light reflecting toward said gloss sensing device at a second intensity;
   comparing said first intensity and said second intensity to determine if said first and second intensities are substantially equivalent; and
   adjusting at least one of the temperature of said roller and the pressure of said roller when said first intensity and said second intensity are not substantially equivalent.

12. The method of claim 11, wherein if said first intensity is greater than said second intensity, said adjusting at least one of the temperature of said roller and the pressure of said roller comprises at least one of decreasing the temperature of said at least one roller and decreasing the pressure of said at least one roller.

13. The method of claim 11, wherein if said first intensity is lesser than said second intensity, said adjusting at least one of the temperature of said roller and the pressure of said roller comprises at least one of increasing the temperature of said at least one roller and increasing the pressure of said at least one roller.

* * * * *